(12) United States Patent
Sebesta et al.

(10) Patent No.: US 11,465,967 B2
(45) Date of Patent: Oct. 11, 2022

(54) PROCESS FOR THE PREPARATION OF ELAFIBRANOR AND NOVEL SYNTHESIS INTERMEDIATES

(71) Applicant: Advitech Advisory and Technologies SA, Lausanne (CH)

(72) Inventors: Petr Sebesta, Brno (CZ); Jiri Stohandl, Bobrová (CZ); Ilaria Ferrando, Lugano (CH)

(73) Assignee: Advitech Advisory and Technologies SA, Lausanne (CH)

( * ) Notice: Subject to any disclaimer, the term of this patent is extended or adjusted under 35 U.S.C. 154(b) by 123 days.

(21) Appl. No.: 16/635,234

(22) PCT Filed: Aug. 4, 2017

(86) PCT No.: PCT/EP2017/069869
§ 371 (c)(1),
(2) Date: Jan. 30, 2020

(87) PCT Pub. No.: WO2019/025017
PCT Pub. Date: Feb. 7, 2019

(65) Prior Publication Data
US 2021/0101866 A1   Apr. 8, 2021

(51) Int. Cl.
*C07C 319/28* (2006.01)
*C07C 47/565* (2006.01)
*C07C 59/215* (2006.01)
*C07C 319/20* (2006.01)

(52) U.S. Cl.
CPC .......... *C07C 319/28* (2013.01); *C07C 47/565* (2013.01); *C07C 59/215* (2013.01); *C07C 319/20* (2013.01); C07C 2601/16 (2017.05)

(58) Field of Classification Search
CPC ..... C07C 51/367; C07C 59/74; C07C 319/20; C07C 323/22
See application file for complete search history.

(56) References Cited

FOREIGN PATENT DOCUMENTS

| WO | 2004/005233 | 1/2004 |
|----|-------------|--------|
| WO | 2005/005369 | 1/2005 |

OTHER PUBLICATIONS

International serch report and writen opinion issued by the EPO for PCT/EP2017/069869 dated Apr. 5, 2018.
International preliminary report on patentability issued by the EPO for PCT/EP2017/069869 dated Feb. 4, 2020.

*Primary Examiner* — Ana Z Muresan
(74) *Attorney, Agent, or Firm* — Silvia Salvadori

(57) ABSTRACT

The present invention relates to a process for the preparation of elafibranor and novel synthesis intermediates.

2 Claims, No Drawings

PROCESS FOR THE PREPARATION OF ELAFIBRANOR AND NOVEL SYNTHESIS INTERMEDIATES

This application is a U.S. national stage of PCT/EP2017/069869 filed on 4 Aug. 2017 the content of which is incorporated herein by reference in its entirety.

TECHNICAL BACKGROUND

Elafibranor is the International Non-proprietary Name (INN) of 2-[2,6-dimethyl-4-[(E)-3-(4-methylsulfanylphenyl)-3-oxoprop-1-enyl]phenoxy]-2-methylpropanoic acid, having the following chemical formula (I)

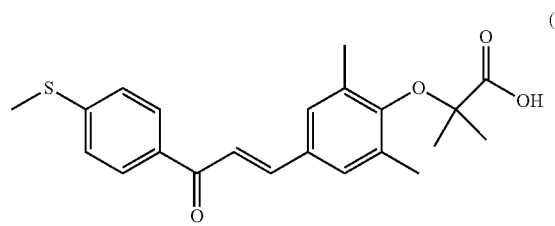

Elafibranor is a drug under evaluation for the treatment of cardiac and metabolic diseases such as diabetes, insulin resistance, dyslipidemia and non-alcoholic fatty liver disease.

Elafibranor was first disclosed in WO2004/005233. In said patent application, a general procedure (General method 4) is disclosed wherein elafibranor could be prepared according to the following Scheme 1

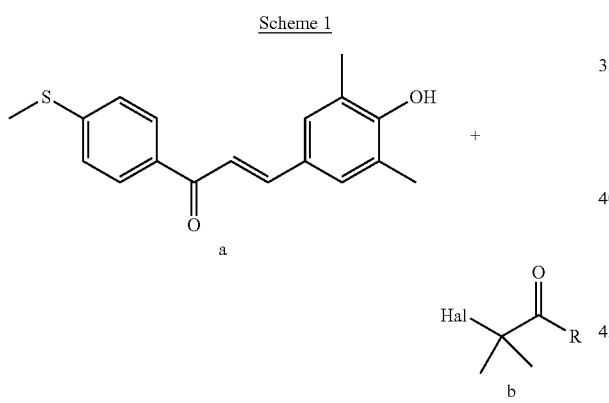

wherein R is O-ethyl or OH, in acetonitrile, in the presence of potassium carbonate.

The present Applicant tried to reproduce the reaction of Scheme 2 wherein R is hydrogen. However, no alkylation occurred in the conditions disclosed in WO2004/005233 and only decomposition of 2-bromo-2-methylpropanoic acid was observed. It results that, in the conditions disclosed in the application, said general procedure can only be carried out when the carboxylic group of compound (b) is esterified. Of course, this implies the additional hydrolyzing step in order to obtain elafibranor.

WO2005/005369 discloses a process for the manufacture of elafibranor which also comprises the process of Scheme 2, wherein R is a protecting group cleavable in acidic conditions, followed by the necessary acidic hydrolysis of said protecting group.

As it will be shown in the following description and examples, the known processes involve many drawbacks.

There is a need to provide novel processes for the preparation of elafibranor, which imply short reactions, limited side reaction, limited reaction steps and give high overall yields.

OBJECTS OF THE INVENTION

It is an object of the invention to provide a new and effective process for the preparation of elafibranor, which implies few reaction steps and which is industrially feasible and cost-effective.

It is a further object of the invention to provide novel synthesis intermediates and their use in the preparation of elafibranor.

DESCRIPTION OF THE INVENTION

According to one of its aspects, the present invention relates to a process for the manufacture of elafibranor of formula (I)

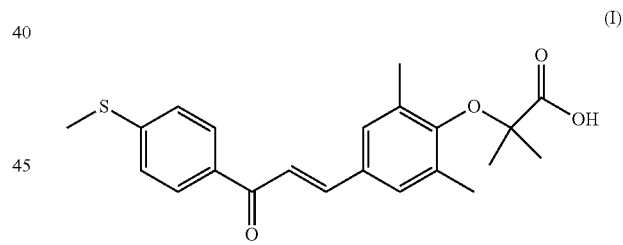

according to the following Scheme 2:

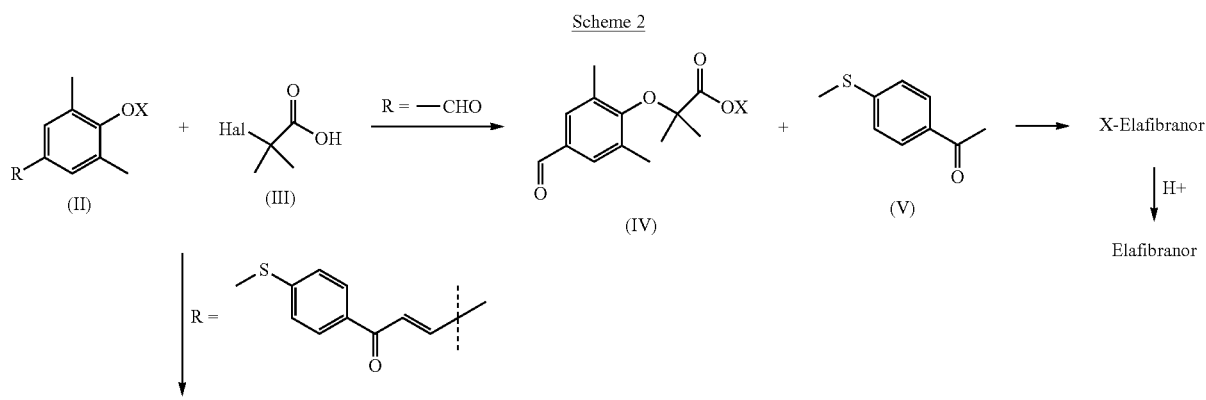

X-Elafibranor

Elafibranor

X = alkali- or alkal-earth imetal  R = ——CHO or

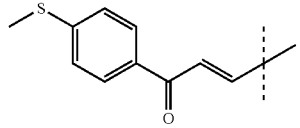

wherein the dotted line indicates the bond by which said group is linked to the remaining part of the molecule.

According to Scheme 2, it is possible to carry out the alkylation reaction on compound (II) when R is —CHO or on compound (II) wherein R is 4-methylthiophenyl-propenyl-2-one. In the first case, a second reaction with compound (V) must be carried out. In this case, it was surprisingly found out that the above synthesis may be performed as a one-pot reaction wherein all compounds (II), (III) and (V) are loaded in the same reaction mixture. The process is carried out in an aprotic solvent which is optionally in admixture with a polar co-solvent. Except for the conversion of elafibranor salt into elafbranor, the process is carried out in basic conditions using a strong base.

So, according to Scheme 2, the invention provides a process for the preparation of elafibranor and its salts, which comprises:
a. mixing compounds (II) and (III)

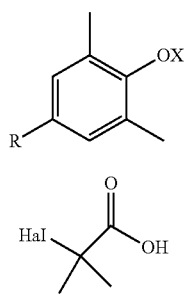

(II)

(III)

wherein
X is an alkali—or a alkali-earth metal
R is —CHO or

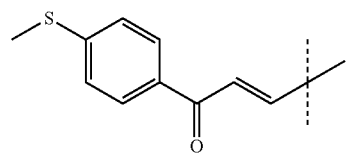

wherein the dotted line indicates the bond by which said group is linked to the remaining part of the molecule; in an aprotic solvent, which is optionally in admixture with a protic co-solvent, in the presence of a strong base;
b. preferably heating the mixture of step (a) and, when R is —CHO, adding 4' (methylthio)acetophenone of formula (V)

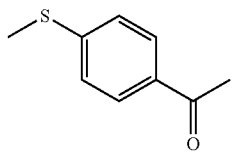

(V)

to the mixture;
c. acidifying the mixture after step (b) with an acidic solution to achieve elafibranor; and
d. optionally isolating and optionally purifying elafibranor thus obtained.

Intermediate compound (IV) does not need to be isolated, however, if needed or desired, it can be prepared, isolated and optionally purified according to the methods known in the art.

Compounds (IIa), (III) and (V) are known in the art.

According to a preferred embodiment, compound (II) is prepared by dissolving a compound of formula (IIa)

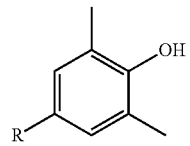

(IIa)

wherein R is as defined in Scheme 2, in an aprotic solvent, in the presence of a strong base, to obtain the compound of formula (II).

According to a preferred embodiment, the process of the invention is a one-pot reaction and comprises the following steps:
a'. in an aprotic solvent comprising (II) or (IIa), optionally in the presence of a protic co-solvent and in the presence of a strong base, preferably sodium or potassium hydroxide;
b'. preferably heating the mixture (a') and adding (III) and, when R is —CHO, also (V);
c'. acidifying the mixture after step (b') with an acidic solution to achieve elafibranor; and
d'. optionally isolating and optionally purifying elafibranor thus obtained.

According to a preferred embodiment, step (b) and (b') is carried out at a temperature of 20 to 70° C., preferably of 45 to 60° C., more preferably of 50 to 55° C.

According to a preferred embodiment, the process of the invention comprises the following steps:

a". dissolving a compound of formula (IIa)

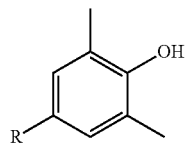

(IIa)

wherein R is as defined in Scheme 2, in an aprotic solvent, optionally in the presence of a protic co-solvent and in the presence of a strong base preferably selected from sodium hydroxide and potassium hydroxide, to obtain the compound of formula (II) as herein defined;

b". heating the mixture of step (a") at a temperature of 20 to 70° C., preferably of 45 to 60° C., more preferably of 50 to 55° C., and adding a solution of 2-halo-2-methylpropanoic acid (III) and, when R is —CHO, also 4'-(methylthio)acetophenone (V);

c". acidifying the mixture after step (b") with an acidic solution to achieve elafibranor, and d". optionally isolating and optionally purifying elafibranor thus obtained.

The purification of elafibranor is preferably carried out by crystallization, more preferably from toluene or from a mixture of toluene and heptane.

According to a preferred embodiment, aprotic solvents are selected from hydrocarbons $C_5$-$C_{12}$-alkanes, alkenes, cycloalkanes and cycloalkenes; aromatic solvents such as toluene and xylenes; halogenated solvents; ketones; esters; heterocyclic solvents such as pyridine; and ethers such as tetrahydrofurane (THF), diethyl ether ($Et_2O$), methyl tert-butyl ether (MTBE), diisopropyl ether (DIPE), dibutyl ether ($Bu_2O$), 1,2-dimethoxyethane (DME). Ethers such as 1,4-dioxane, THF and their mixtures are preferred, THF being most preferred.

A polar solvent may be present in the reaction mixture of the process of the invention, as a co-solvent. Preferably, polar aprotic solvents are selected from dimethylformamide (DMF), dimethylacetamide (DMA), acetonitrile, dimethyl sulfoxide (DMSO), sulfolane, N-methyl-2-pyrrolidone (NMP), 1,3-dimethyl-2-imidazolidinone (DMI), hexamethylphosphoramide (HMPA), N,N'-dimethylpropyleneurea (DMPU). Preferably, polar protic solvents are selected from water, alcohols, diols and their mixtures, acetonitrile, sulfolane, n-propanol and 1,4-butandiol are preferred, n-propanol being more preferred.

According to a preferred embodiment, when R is —CHO, a polar co-solvent is also present in the reaction mixture, preferably a polar aprotic co-solvent.

Ratios (vol/vol) of aprotic solvent to polar solvent are preferably, but not limited to, approx. 4:1 for n-propanol, approx. 9:1 for 1,4-butandiol and approx. 20:1 for water, acetonitrile and sulfolane.

The strong base used in the process of the invention is selected from hydroxides, alkoxides, hydrides, amides, diethylamides, diisopropylamides, tetramethylpiperidides and hexamethyl disilazides of alkali metals and alkaline earth metals or strong organic bases such as N,N-diisopropylethylamine, DBU, DBN, quinuclidine, DABCO, Barton base or other guanidine derivatives, and phosphazene bases.

Sodium and potassium hydroxides are preferred strong bases, preferably sodium hydroxide, advantageously solid sodium hydroxide, such as powdered, pellets, flakes, and bead sodium hydroxide; particularly preferred is pulverized solid sodium hydroxide.

According to a preferred embodiment, the process is carried out under vigorous stirring.

The reaction is completed in a very short time, such as 1 to 6 hours, generally 2-3 hours. The skilled man is anyway perfectly able to check the development of the reaction, for instance by using chromatographic techniques.

According to a preferred embodiment, when the reaction of step (b), (b') and (b") is completed, a basic aqueous solution is added, for instance an aqueous solution of sodium hydroxide and the organic solvent is distilled off.

The mixture is the worked up according to the methods known in the art to provide elafibranor sodium or potassium salt, which is converted to elafibranor by acidification. Examples of work up techniques are provided in the Experimental Section, as illustrative examples of the invention.

With respect to the starting compound (IIa) wherein R is 4-methylthiophenyl-propenyl-2-one, the base, preferably a hydroxide, is preferably used in a molar excess, such as for example in a 2.5-5 molar excess, more preferably in about a 3.5 molar excess, while compound (III) is preferably used in a 1.5-5 molar excess, more preferably in about a 2-3 molar excess.

When in compound (IIa) R is —CHO, the same above mentioned molar excesses are can be used for the hydroxide and for compound (III), whereas compound (V) is preferably used in an equimolar amount.

The process of the invention gives high yields and a very pure final product.

According to a preferred embodiment, R is —CHO.

According to a preferred embodiment, R is —CHO and the strong base is sodium hydroxide.

According to a preferred embodiment, R is —CHO, the strong base is sodium hydroxide and the solvent is THF, optionally with a polar co-solvent, preferably n-propanol.

With respect to the prior art processes, the process of the invention provides the following advantages:
  less steps, thus being cost-effective;
  lower excess of alkylation reagent (1.7 3.0 equiv. of 2-bromo-2-methylpropanoic acid vs. 6-10 equiv. of alkyl 2-bromo-2-methylpropanoate equivalents used in WO2004/005233, General method 4.
  avoiding poly(alkyl methacrylate) formation;
  shorter reaction times;
  higher overall yields.

Also, compared to the known processes, the process of the invention provides limited side reactions, such as elimination, oxidative dimerization, ether hydrolysis, Nazarov reaction, which may occur with the prior art processes, such as the following:

Elimination and polymerization

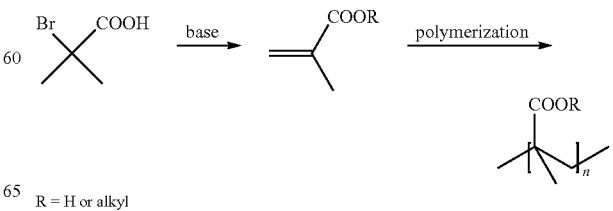

R = H or alkyl

Ether hydrolysis

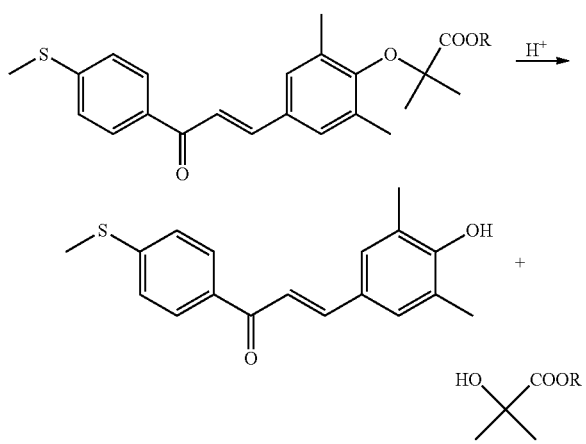

Nazarov cyclization

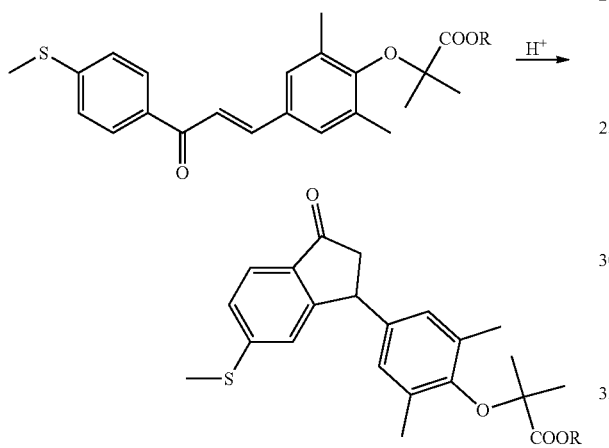

Indeed, without willing to be bound to any theory, applicant deems that the basic principle of new process is limited solubility of phenolates and salts of organic acids in non-polar (hydrocarbons, toluene) and borderline polar solvents (ethers, ketones, esters, halogenated solvents). In the first step, sodium phenolate is precipitated from solution of phenol (IIa) by sodium hydroxide and forms suspension. Then solution of 2-bromo-2-methylpropanoic acid (together with (V)) is added and sodium salt of this acid precipitates from the solvent and suspension of sodium phenolate and sodium 2-bromo-2-methylpropanoate is formed.

When a weaker base (for example potassium carbonate) is used, formation of phenolate does not take place but the weaker base is usually still strong enough to trigger main side reaction—elimination, which is a severe inconvenience, either for the good outcome of the process and due to health hazard issues. In fact, the repeated exposure can lead to serious health problems.

As already mentioned the solubility of phenolate and salt of acid is limited. It means that most of the stuff is in unreactive solid form but little part remains dissolved and ready to perform formation of intermediate (IV). Intermediate (IV) is also salt of carboxylic acid and precipitates from non-polar and borderline polar solvents even more willingly than phenolate (II) and salt of (III). Precipitation of intermediate (IV) is a driving force of the reaction as it shifts the equilibrium towards the desired product.

It is therefore evident that the process of the invention provides a great technical improvement when compared to the prior art.

According to another of its aspects, the invention relates to the compounds of formula (II) and (IV) wherein X is Na, preferably compounds of formula (II) and (IV) wherein R is —CHO. Said compounds may be prepared as above disclosed and are particularly useful in, but not limited to, the preparation of elafibranor.

The invention will be illustrated in the following examples, which are not at all to be considered as limitative.

EXPERIMENTAL SECTION

Example 1

One Pot Synthesis of 1-[(4-methylthio)phenyl]-3-[(3,5-dimethyl-4-carboxydimethyloxy)phenyl]prop-2-en-1-one (Elafibranor) Performed as a Multicomponent Reaction

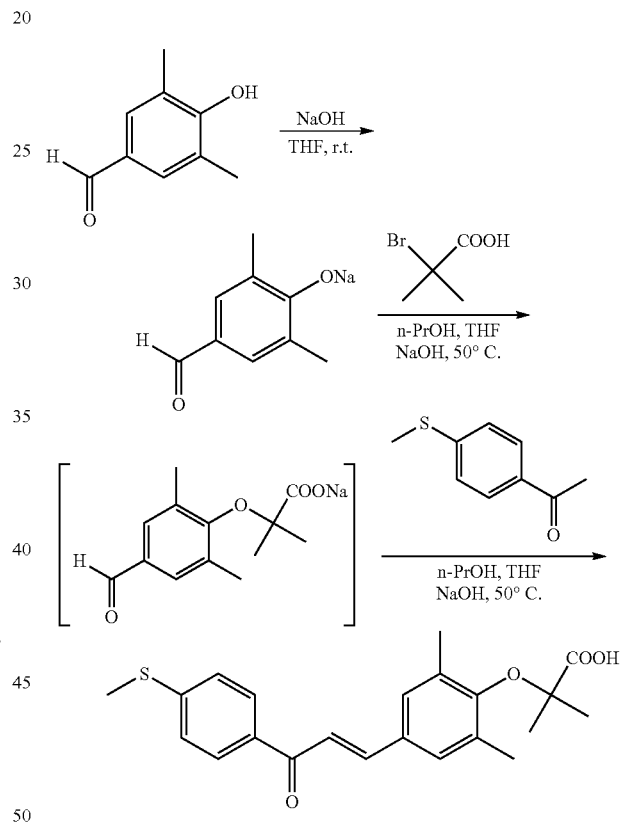

4-hydroxy-3,5-dimethylbenzaldehyde (300 mg; 2.0 mmol) was dissolved in THF (6 mL), pulverized NaOH (360 mg 9.0 mmol; 4.5 equiv.) was added and mixture was stirred until sodium phenolate was formed as a greenish yellow suspension. 1-propanol (2 mL) was added, suspension was heated to 50° C. and a solution of 2-bromo-2-methylpropanoic acid (1002 mg, 6.0 mmol; 3 equiv.) and 4-(methylthio)acetophenone (332 mg; 2.0 mmol; 1 equiv.) in THF (2 mL) was added over approximately 20 minutes. After the addition, the mixture was held at 50° C. for 2 h and solution of NaOH (400 mg; 10 mmol; 5.0 equiv.) in water (10 mL) was added. Reaction mixture was heated to reflux (66-67° C.), THF was distilled off and reaction was quenched by addition of 1M HCl to pH=3.0-3.5. The mixture was taken up into MTBE and extracted with 1M Na$_2$CO$_3$. The sodium salt of product, obtained by salting out after addition of appropriate amount of NaCl, was dissolved in water, acidified with 1M HCl to pH 2.0 and extracted with toluene. The product was obtained after concentration of toluenic solution under vacuum and crystallization as a yellow solid. Isolated yield: 61%, HPLC purity: 99.4%.

$^1$H NMR (DMSO): δ 1.42 (s, 6H, C(C$\underline{H}_3$)$_2$), 2.25 (s, 6H, Ph-C$\underline{H}_3$), 2.57 (s, 3H, S—C$\underline{H}_3$), 7.40 (m, 2H, H$_{Ar}$), 7.56 (s, 2H, H$_{Ar}$), 7.64 (d, J=15.5 Hz, 1H, CO—CH=C$\underline{H}$-Ph), 7.82 (d, J=15.7 Hz, 1H, CO—C$\underline{H}$=CH-Ph), 8.11 (m, 2H, H$_{Ar}$), 12.95 (s, 1H, COO$\underline{H}$).

$^{13}$C NMR (DMSO): δ 13.94 (S-$\underline{C}$H$_3$), 17.53 (2Ph-$\underline{C}$H$_3$), 24.98 (C($\underline{C}$H$_3$)$_2$), 80.68 (O—$\underline{C}$(CH$_3$)$_2$—COOH), 120.82 (CO—$\underline{C}$H=CH-Ph), 124.90 (2C$_{Ar}$H), 128.98 (2C$_{Ar}$H), 129.30 (2C$_{Ar}$H), 130.19 (C$_{Ar}$), 133.13 (2C$_{Ar}$), 133.89 (C$_{Ar}$), 143.31 (CO—CH=$\underline{C}$H-Ph), 145.37 (C$_{Ar}$—S), 154.93 (C$_{Ar}$—O), 174.96 (COOH), 187.77 (C=O).

HRMS (ESI+) m/z [C$_{22}$H$_{25}$O$_4$S]$^+$: calcd 385.1474; found 385.1470.

Comparative Examples According to WO2004/005233 (General Method 4)

Comparative Example A

Preparation of Methyl 2-(4-formyl-2,6-dimethylphenoxy)-2-methylpropanoate According to WO2004/005233

4-hydroxy-3,5-dimethylbenzaldehyde (150 mg; 1.0 mmol) was dissolved in acetonitrile (5 mL), potassium carbonate (691 mg; 5.0 mmol; 5 equiv.) and a solution of methyl 2-bromo-2-methylpropanoate (543 mg; 3.0 mmol; 3 equiv.) in acetonitrile (5 mL) were added. The reaction mixture was briskly stirred under reflux for 3 hrs, then the second portion of methyl 2-bromo-2-methylpropanoate (543 mg; 3.0 mmol; 3 equiv.) was added and the reaction mixture was stirred for additional 3 hrs. LC-MS analysis showed almost complete conversion to methyl 2-(4-formyl-2,6-dimethylphenoxy)-2-methylpropanoate.

Comparative Example B

Preparation of 2-(4-formyl-2,6-dimethylphenoxy)-2-methylpropanoic Acid According to WO2004/005233

4-hydroxy-3,5-dimethylbenzaldehyde (150 mg; 1.0 mmol) was dissolved in acetonitrile (5 mL), potassium carbonate (691 mg; 5.0 mmol, 5 equiv.) and a solution of 2-bromo-2-methylpropanoic acid (1002 mg; 6.0 mmol; 6 equiv.) in acetonitrile (5 mL) were added. The reaction mixture was briskly stirred under reflux for 3 hrs, then water (5 mL) was added to homogenize the mixture. LC-MS analysis showed that 2-bromo-2-methylpropanoic acid is completely converted to 2-methylacrylic acid, required product—2-(4-formyl-2,6-dimethylphenoxy)-2-methylpropanoic acid—was not found in the reaction mixture.

Comparative Example C

Preparation of 2-(4-formyl-2,6-dimethylphenoxy)-2-methylpropanoic Acid According to WO2004/005233

4-hydroxy-3,5-dimethylbenzaldehyde (150 mg; 1.0 mmol) was dissolved in acetonitrile (5 mL), potassium carbonate (691 mg; 5.0 mmol; 5 equiv.) and a solution of 2-bromo-2-methylpropanoic acid (1670 mg; 10.0 mmol; 10 equiv.) in acetonitrile (5 mL) were added. The reaction mixture was briskly stirred under reflux for 3 hrs, then water (5 mL) was added to homogenize the mixture. LC-MS analysis showed that 2-bromo-2-methylpropanoic acid is completely converted to 2-methylacrylic acid, required product—2-(4-formyl-2,6-dimethylphenoxy)-2-methylpropanoic acid—was not found in the reaction mixture.

The invention claimed is:
1. A one-pot process comprising the following steps:
   a'. in an aprotic solvent comprising compound (II) or (IIa),

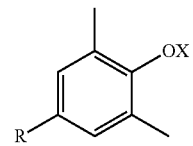

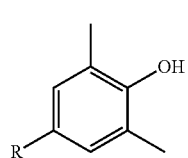

wherein X is an alkali or an alkali-earth metal;
R is —CHO or

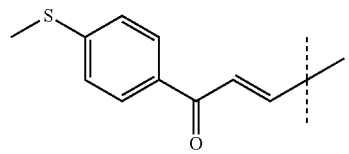

optionally in the presence of a protic co-solvent and in the presence of a strong base comprising sodium or potassium hydroxide thus obtaining a mixture;
   b'. optionally heating the mixture and adding (III)

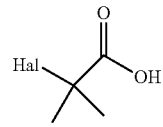

and, when R is —CHO adding 4'-(methylthio)acetophenone of formula (V)

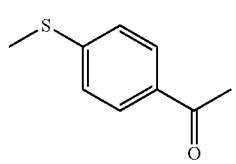

c'. acidifying the mixture after step (b') with an acidic solution to achieve elafibranor; and
   d'. optionally isolating and optionally purifying elafibranor thus obtained.

2. The process according to claim 1 comprising:

a". dissolving a compound of formula (IIa)

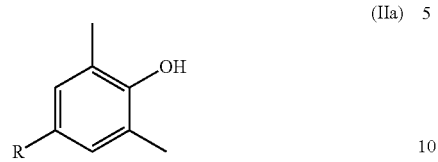

wherein R is as defined in claim 1, in an aprotic solvent, optionally in the presence of a protic co-solvent and in the presence of a strong base comprising sodium hydroxide and potassium hydroxide, to obtain the compound of formula (II) as defined in claim 1;

b". heating the mixture of step (a") at a temperature of 20 to 70° C., and adding a solution of 2-halo-2-methyl-propanoic acid (III), when R is —CHO, also 4'-(methylthio)acetophenone (V);

c". acidifying the mixture after step (b") with an acidic solution to achieve elafibranor, and d". optionally isolating and optionally purifying elafibranor thus obtained.

* * * * *